(12) United States Patent
St Amant, III

(10) Patent No.: US 10,126,214 B1
(45) Date of Patent: Nov. 13, 2018

(54) WET GAS SAMPLING SYSTEM AND METHOD THEREFORE

(71) Applicant: Mayeaux Holding LLC, Gonzales, LA (US)

(72) Inventor: Valmond Joseph St Amant, III, St Amant, LA (US)

(73) Assignee: Mayeaux Holding, LLC, Gonzales, LA (US)

( * ) Notice: Subject to any disclaimer, the term of this patent is extended or adjusted under 35 U.S.C. 154(b) by 158 days.

(21) Appl. No.: 14/805,230

(22) Filed: Jul. 21, 2015

Related U.S. Application Data

(60) Provisional application No. 62/027,098, filed on Jul. 21, 2014.

(51) Int. Cl.
*G01N 1/28* (2006.01)
*G01N 9/32* (2006.01)

(52) U.S. Cl.
CPC .................. *G01N 1/28* (2013.01); *G01N 9/32* (2013.01)

(58) Field of Classification Search
CPC ......... B01L 2300/14; B01L 7/00; G01N 1/02; G01N 2001/105; G01N 1/10
See application file for complete search history.

(56) References Cited

U.S. PATENT DOCUMENTS

| | | | |
|---|---|---|---|
| 5,538,344 A | 7/1996 | Dybdahl | |
| 7,637,151 B2 * | 12/2009 | Raghuraman | G01N 33/2823 250/255 |
| 7,716,994 B2 | 5/2010 | Mattar et al. | |
| 7,717,000 B2 | 5/2010 | Xie et al. | |
| 7,942,065 B2 | 5/2011 | Xie | |
| 8,271,248 B2 * | 9/2012 | Pomerantz | E21B 49/00 703/10 |
| 8,436,116 B2 * | 5/2013 | Akhoury | C07C 29/76 526/240 |
| 9,194,974 B2 * | 11/2015 | Roy | G01V 3/38 |
| 9,682,373 B2 * | 6/2017 | Losada | B01L 3/50215 |
| 2002/0167314 A1 * | 11/2002 | Prammer | G01N 24/081 324/303 |
| 2007/0214877 A1 * | 9/2007 | Shammai | E21B 49/10 73/152.24 |
| 2008/0083268 A1 * | 4/2008 | Hammami | B01L 3/502 73/54.01 |
| 2008/0141767 A1 * | 6/2008 | Raghuraman | G01N 33/2823 73/152.55 |
| 2008/0190178 A1 * | 8/2008 | Hammami | B01L 3/502 73/54.01 |

(Continued)

OTHER PUBLICATIONS

John M. Campbell & Co, Transportation of Natural Gas in Dense Phase, www.jmcampbell.com/tip-of-the-month/, Jan. 2010.

(Continued)

*Primary Examiner* — David A Rogers
(74) *Attorney, Agent, or Firm* — Joseph T Regard, Ltd plc

(57) ABSTRACT

A system for on-stream sampling of pressurized process fluid such as natural gas or the like, said pressurized process fluid in the form of gas having liquid entrained therein, or otherwise referenced as multiphase or "wet". The preferred embodiment of the present invention contemplates a system for obtaining an accurate sample of said process gas in such a manner as to avoid the inherent problems with multi-phase gas streams, via sampling said multi-phase gas stream in its dense phase.

27 Claims, 11 Drawing Sheets

(56) References Cited

U.S. PATENT DOCUMENTS

| | | | |
|---|---|---|---|
| 2008/0190180 A1* | 8/2008 | Zougari | G01N 33/2823 73/61.62 |
| 2009/0031827 A1* | 2/2009 | Al-Qassem | G01N 1/10 73/863.02 |
| 2009/0235731 A1* | 9/2009 | Zuo | E21B 49/08 73/152.28 |
| 2009/0312997 A1* | 12/2009 | Freed | E21B 49/00 703/10 |
| 2010/0077874 A1* | 4/2010 | Kanomata | B01D 11/0203 73/863.21 |
| 2013/0204533 A1* | 8/2013 | Goodwin | E21B 49/10 702/9 |
| 2013/0241099 A1* | 9/2013 | Losada | B01L 3/50215 264/46.9 |
| 2013/0243028 A1* | 9/2013 | Singh | G01N 33/2823 374/43 |
| 2013/0263680 A1* | 10/2013 | Barere | F17C 7/04 73/863.12 |
| 2013/0289961 A1* | 10/2013 | Ray | E21B 47/00 703/10 |
| 2014/0343909 A1* | 11/2014 | Guerillot | G01V 11/00 703/2 |
| 2015/0120255 A1* | 4/2015 | King | E21B 43/00 703/2 |
| 2016/0319640 A1* | 11/2016 | Ratulowski | E21B 49/00 |

OTHER PUBLICATIONS

John M. Campbell & Co, Variation of properties in the dense phase region, Part 1—Pure Compounds, www.jmcampbell.com/tip-of-the-month/, Dec. 2009.

Expro Petrotech Metering Services, Petrotech Isosplit Separator Sampling, http://exprogroup.com/media/13425/M1003-IsoSplit-Separator-Sampling-v02.pdf, Info Sheet Rev Dec. 2012.

US Energy Information Administration, What are Natural Gas Liquids and How are They used?, http://www.eia.gov/todayinenergy/detail.cfm?id=5930, Apr. 20, 2012.

* cited by examiner

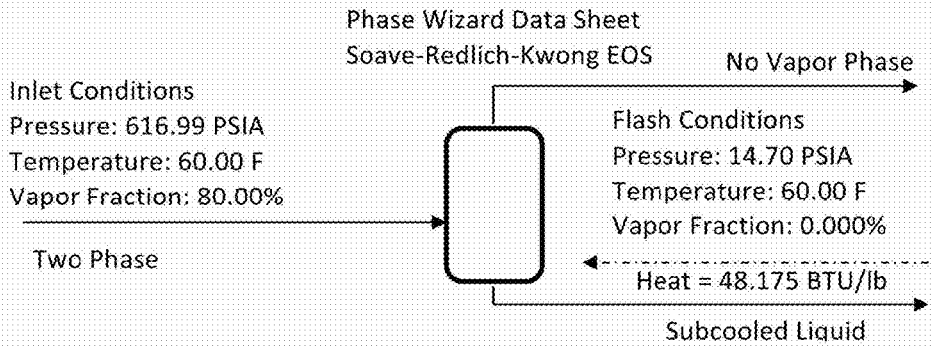

| Stream Properties | Inlet | Vapor | Liquid |
|---|---|---|---|
| Condition | Two Phase | Empty | Subcooled |
| Percent of Feed – molar | 100.00 | | 100.00 |
| Percent Vapor – molar | 80.00 | | 0.000 |
| Pressure – PSIA | 616.99 | | 14.70 |
| Temperature – F | 60.00 | | 60.00 |
| Volume - ft3/lb | 0.2397 | | 0.0515 |
| Density – lb/ft3 | 4.173 | | 19.433 |
| ZFactor | 0.7168 | | 0.9944 |
| Average Mol Wgt | 26.864 | | 26.864 |
| Enthalpy – BTU/lb | 131.895 | | 180.070 |
| Entropy – BTU/lb-F | 1.635 | | 1.692 |
| Heat Capacity – BTU/lb-F | 0.4630 | | 0.4425 |
| Viscosity – centipoise | 0.0308 | | 0.0165 |
| Thermal Conductivity – BTU/ft-F | 0.0455 | | 0.1085 |
| Surface Tension – dynes/cm | 8.5949 | | 2.5821 |
| Ideal Net Heat of Combustion – BTU/SCF | 1362.40 | | 1362.40 |
| Critical Temperature – F | 67.44 | | 67.44 |
| Critical Pressure – PSIA | 1896.36 | | 1896.36 |
| Component Mole Percents | | | |
| Nitrogen | 4.000 | | 4.000 |
| Carbon Dioxide | 1.200 | | 1.200 |
| Methane | 63.600 | | 63.600 |
| Ethane | 10.200 | | 10.200 |
| Propane | 7.900 | | 7.900 |
| Isobutane | 2.100 | | 2.100 |
| n-Butane | 6.200 | | 6.200 |
| Isopentane | 1.800 | | 1.800 |
| n-Pentane | 2.200 | | 2.200 |
| n-Hexane | 0.5100 | | 0.5100 |
| n-Heptane | 0.1800 | | 0.1800 |
| n-octane | 0.0800 | | 0.0800 |

FIG 3

WET GAS SAMPLING SYSTEM AND METHOD THEREFORE

BENEFIT CLAIM

The present application claims the benefit of U.S. Provisional Patent Application Ser. No. 62/027,098, filed Jul. 21, 2014, entitled WET GAS SAMPLING SYSTEM AND METHOD THEREFORE, listing as inventor Valmond Joseph St Amant.

FIELD OF THE INVENTION

The present invention relates to sampling of pressurized process fluids, and in particular to a system for on-stream sampling of pressurized process fluid such as natural gas or the like, said pressurized process gas having liquid entrained therein, or otherwise referenced as multiphase or "wet". The preferred embodiment of the present invention contemplates a system for obtaining an accurate sample of said process gas in such a manner as to avoid the inherent problems with multi-phase gas streams, by sampling said multi-phase gas stream in its dense phase.

BACKGROUND OF THE INVENTION

Natural gas is bought and sold based on its heating value. It is the BTU content that determines the monetary value of a given volume of natural gas. This BTU value is generally expressed in decatherms (one million BTU). In the determination of total heat value of a given volume of gas, a sample of the gas is analyzed and from the composition and its heat value per unit volume is calculated. This value is generally expressed in BTU/cu ft. The typical range of transmission quality gas ranges between 1000 and 1100 BTU/cu ft. Production gas, storage facility gas, NGL, and Shale Gas can have much higher heating values up to, or even exceeding, 1500 BTU/cu ft.

There has been a long standing controversy between gas producers and gas transporters regarding entrained liquid typically present in most high BTU/cu ft gas (rich or wet gas). Transporter tariffs require essentially liquid-free gas. Hydrocarbon liquid in the gas being transported causes operational and safety problems. The practice is to separate the liquid before entering a transport (pipe) line.

The American Petroleum Institute (API) 14.1 standards (Manual of Petroleum Measurement Standards, 2006) scope does not include "wet gas" "(a term referenced by the Natural Gas industry as a gas that is at its hydrocarbon dew point temperature and/or contains entrained liquid), nor does the GPA 2166 standard (Obtaining Natural Gas Samples for Analysis by Gas Chromatography, 2005). In summary, there is no known standard which defines how to obtain a "representative sample" of a natural gas supply having entrained hydrocarbon in any form.

The liquid hydrocarbon (HC) content of a Natural gas is comprised mainly of the heavier (higher molecular weights such as propane, ethane and butane) components. As indicated by the U.S. Energy Information Administration, in discussing Natural Gas Liquids (NGLs):

"Oil and natural gas producers are increasingly targeting liquids-rich parts of supply basins due to higher crude oil prices, which influence the value of NGLs. NGL field production is growing in the United States, representing an important part of the supply picture. NGLs are extracted from the natural gas production stream in natural gas processing plants. Current elevated levels of domestic oil and gas development have pushed NGL production to an all-time high, leading to concerns over processing and distribution constraints in the coming years. Ethane, propane, butane, isobutane, and pentane are all NGLs.", from www.eia.gov/todayinenergy/detail.cfm?id=5930

Accordingly, the heating value of NGLs can be quite high when compared to dry natural gas, and therefore NGLs or liquid hydrocarbons (HC) can have great monetary value. This is the reason that producers wish to have the liquid HC represented in the sample composition utilized for computing the BTU/cu ft content.

American Petroleum Institute (API) 14.1 standard indicates:

"2. Purpose and Scope

The purpose of this standard is to provide a comprehensive guideline for properly collecting, conditioning, and handling representative samples of natural gas that are at or above their hydrocarbon dew point . . .

. . . This standard does not include sampling multiphase flow (free liquid and gas) or supercritical fluids."

API 14.1 standard, Appendix B section B-3 Multiphase Flow states that:

"Sampling of multiphase flow is outside the scope of this standard. Sampling of multiphase (gas and liquid) mixtures is not recommended and should be avoided if at all possible. In the multiphase flow, the ideal system would mix the gas and liquid flows uniformly and collect a sample of the true mixture flowing in the line by using a properly designed sample probe and an isokinetic sampling system. Current technology of natural gas sampling is not sufficiently advanced to accomplish this with reasonable accuracy. When sampling a multiphase liquid-gas flow, the recommended procedure is to eliminate the liquid from the sample. The liquid product that flows through the line should be determined by another method. The liquid fraction of the multiphase flow may contain water and hydrocarbons. The hydrocarbons can contribute significantly to the energy (measured in British thermal units) content of the gas and their presence in the gas line must not be overlooked."

The Gas Processors Association (GPA) 2166 standard's scope states that the standard is not designed for sampling Natural gas that is at, or below, its HC dew point temperature. Within the body of this standard, several references are made to avoiding liquid entrainment and condensation, due to its impact on sample composition and the calculated heat value.

The API 14.1 and GPA 2166 are the primary standards utilized by most Gas companies to guide their sampling methods. These standards specifically exclude the taking of Natural gas samples representing a combined gas and liquid, nor do they specify or advocate the taking of samples from a supercritical (dense phase) fluid stream.

Rather, the API standard specifies that, ideally, one would mix the gas and liquid flows in a multiphase stream uniformly, and collect a sample of the true mixture flowing in the line, by using a properly designed sample probe coupled with an isokinetic sampling system. However, there is currently no known technology available in the natural gas sampling arts to provide such a system which could accomplish this within acceptable parameters, particularly as to accuracy.

There have been many attempts to achieve the representative sampling of Natural gas/HC liquid mixture. Most methods use a dynamic flow isokinetic technique following homogenization via a homogenizing mixer or the like. In an ideal world, gas having perfectly mixed liquid droplets in representative suspension would be directed into the entrance port of a sample probe (isokinetic probe), without a change of velocity or direction of liquid droplets.

To accomplish this particular technique, the supply gas velocity must be known, 1) the gas velocity at the probe entrance must be maintained equal to the supply gas velocity, and 2) the probe entry design must be shaped such as not to disturb the flow pattern of the liquid droplets. This approach, even under closely controlled conditions, is not believed accurate enough for custody transfer measurement under current API standards. Therefore, it is neither a good nor a practical method for sampling wet gas on an "ongoing" basis.

Additionally, there are two other forms of liquid which may be present in the transport line other than suspended liquid droplets. One form is a liquid film which is always present when suspended droplets are flowing with the gas stream. Another form is liquid which at times flows along the bottom of the transport pipe. It is generally not known how the liquid is distributed between these three forms, and additionally, the distribution is dynamic and can be ever changing, even at the same location.

Further, measurement of only the suspended droplets generally will not generally provide an accurate indication of the total liquid present in the transport line, and thus the reason a "perfect" homogenizing mixer would be required for an accurate analysis. But such a "perfect" mixer is not believed to exist, as such a device would have to perform accurately notwithstanding varying distributions not only at one designated location, but also at various locations and with varying amounts and distributions of liquids in the fluid stream, with varying compositions as well as contaminates, flows and pressures, etc.

The Petrotech company of Kvala, Norway (hereinafter PETROTECH) utilizes an isokinetic Natural gas technique called ISOSPLIT®. The method consists of static mixing the two phases followed by dynamic isokinetic sampling of the resulting mixture. As previously stated, this technique is difficult to execute, and can produce less than desirable results. It is primarily employed at the well head. The PETROTECH U.S. Pat. No. 5,538,344 relates primarily to the positioning of a mixing body within a pipeline.

The oilfield services company Schlumberger of Sugar Land, Tex. uses a flow conditioner to attempt to homogenize or mix the two phase sample followed by independent flow measurement of the individual phases and using that information in measuring the total flow isokinetically or by measuring the pressure differential to infer and control the flow measurement. See U.S. Pat. Nos. 7,717,000 and 7,942,065.

A third company, Invensys (now Schneider Electric, based in France) uses two different flow measurement techniques to measure separately the dry gas (a differential pressure flowmeter) and the wet gas (by a Coriolis flowmeter). See U.S. Pat. No. 7,716,994.

In conclusion, the above isokinetic sampling systems are designed to insure an isokinetic fluid flow of process gas into the opening of a probe and therethrough to an external location. With such a configuration, the fluid stream velocity must be known and the fluid velocity entering the probe must be controlled, as well as having a perfectly mixed homogenized sample, which makes the technique generally impractical for typical field sampling of fluids.

GENERAL SUMMARY DISCUSSION OF THE INVENTION

Unlike the above prior art dynamic isokinetic sampling systems, which are universally believed to require a mechanical mixer or separator for accurate sampling of the multiphase fluid stream, the present invention teaches a new and innovative "dense" sampling technique which dispenses with the requirement of such mixing/separating, by exploiting a heretofore little understood fluid phase heretofore believed unused in the fluid sampling art.

The present invention is particularly suitable for use in sampling higher pressure sources such as the newly discovered Shale Gas, deep water natural gas, natural gas in storage facilities, as well as natural gas containing NGL, which can typically have a pressure in excess of 1,000 PSIG, while comprising a multiphase fluid stream and, depending upon the pressure and temperature, can be "wet", or contain entrained liquids in the fluid stream.

The present invention provides a far superior sampling solution for wet gas streams, which traditionally have been difficult to sample dynamically due to the multi-phase nature and composition, including the new methodology of manipulating the flow to provide a "dense" phase sample via flow, pressure, and/or temperature, so as to provide a homogenized, "dry" sample composition without the need to of traditional mechanical mixing/separating techniques.

Referring to FIG. 1, the aforementioned "wet" gas compositions do not have the typical stream composition of traditional quality gas as historically transported via pipeline or the like. For example, the composition listed in said FIG. 1 for "wet" gas does not have the typical transmission quality gas methane concentration of 90% Methane. Instead, as indicated in FIG. 1, it is only about 64% Methane.

Furthermore, heavier hydrocarbons such as Ethane, Propane, and Butane (NGL) are present in significant quantities causing the gas to be "wet", or containing liquid at pressures and temperatures inside the two phase region of the phase diagram of FIG. 1, at pressures in the 1,000 PSIG (1,014.7 PSIA) to 1,900 PSIG (1,914.7 PSIA) at the most common process temperatures, as well as most ambient temperatures. At pressures above the Critical Point (CP), the sample becomes dense phase.

Continuing with FIG. 2, this chart illustrates that if the sample composition of FIG. 1 was at 156.59 PSIA (141.89 PSIG) and 60 degrees F., it would contain approximately 95% gas and 5% liquid.

But if the sample composition was at 619.99 PSIA (605.29 PSIG) and 60 degrees F., as shown in FIG. 3, the same sample composition (of FIGS. 1 and 2) would contain approximately 80% gas and 20% liquid.

Natural Gas companies have begun to understand that controlling the pressure of these "wet" gas streams to facilitate pipeline transmission in a "dense" phase has its advantages, as set forth indicated in the quote from a December 2009 "tip of the month" (found a www.jmcampbell.com) from John M. Campbell & Co, an operator training company in the gas conditioning and processing field:

"For a pure compound above critical pressure and critical temperature, the system is often times referred to as a "dense fluid" or "supercritical fluid" to distinguish it from normal vapor and liquid. "Dense" phase is a fourth (Solid, Liquid, Gas, "Dense") phase that cannot be described by the senses. Pipelines are being built to transport CO2 and natural gas in the "dense" phase region due to its higher density, and this also provides the added benefit of no liquids formation in the pipeline."

Accordingly, it can be averred that the transportation side of the natural gas industry may have some limited understanding of dense phase multiphase fluid streams and possible advantages in exploiting same in fluid pipeline transmission, but there is no such understanding or recognition believed present in the sampling industry as would be used in sampling processes, methodologies, techniques, or devices.

In fact, not only does the prior art not contemplate, suggest, or otherwise evidence an understanding appreciation of the use dense phase in a fluid stream for sampling of wet gas or multiphase fluid streams, the known prior art sampling techniques and standards teach a wholly different methodology for treating such "wet" gas when sampling, for the most part generally requiring: 1) the mechanical mixing of the two phases to facilitate a homogenous mixture; or 2) mechanically separating the two phases.

As discussed in the General Background section above, current industry standards for sampling are for vapor phase only, and not multiphase or supercritical fluids, which are considered outside accepted industrial sampling standards, and thus are not recommended.

In fact, current API standards recommend the use of Equation of State (EOS) software such as can be found at www.nist.gov/srd/nist23.cfm for the purpose of ensuring that a sample is vapor phase only, as well as the need to prevent the sample from condensing to liquid. Such industrial standards have not suggested, contemplated, or otherwise recognized that EOS software could be used to provide a guideline for forced transition to dense phase for sampling purposes; in fact, no such recognition of dense phase is evidenced, and dense phase for sampling purposes is unknown and considered outside the scope of said API standards. For Example, See API 14.1 2006, Section 2 Purpose and Scope, which specifically indicates that:

"This standard does not include sampling multi-phase flow (free liquid and gas) or supercritical fluids."

Further, Section B.3 Multiphase Flow of Chapter 14 of Natural Gas Fluids Measurement of the API 14 states specifically that:

"Sampling of multiphase (gas and liquid) mixtures is not recommended and should be avoided if at all possible. In the multiphase flow, the ideal system would mix the gas and liquid flows uniformly and collect a sample of the true mixture flowing in the line by using a properly designed sample probe and an isokinetic sampling system. Current technology of natural gas sampling is not sufficiently advanced to accomplish this with reasonable accuracy."

See also Section 5 of API 14.1 2006, which relates to sampling of gas streams of unknown hydrocarbon dew point and composition, Section 6.3.1 (Phase Changes), 6.4 (Revaporization), Appendix A (The Phase Diagram), A.5 (Natural Gas Mixture Phase Diagrams), and A.6 (Limitations of Phase Diagram), the contents of which are incorporated herein by reference thereto.

While such a finding was understandable considering the present state of technology implemented and the obsolete view that dry gas is desirable over wet gas view of earlier productions, which provided insufficient value to the liquid component to justify homogenization and sampling, such a standard is now respectfully averred as being obsolete in view of the rich energy potential found in the aforementioned wet gases, which provide multiphase fluid flows containing such high liquid BTU potential, that they cannot be disregarded. This is especially true because the present invention provides a viable, precise and effective means of sampling via phase change to dense phase, without having to rely upon the old mechanical means of separation or mixing, now obsolete, as still used today.

As indicated in the International Association for the Properties of Water and Steam, 2007:

"The term critical point is sometimes used to specifically denote the vapor-liquid critical point of a material, above which distinct liquid and gas phases do not exist. This is the point at which the phase boundary between liquid and gas terminates. In water, the critical point occurs at around 647 K (374° C.; 705° F.) and 22.064 MPa (3200 PSIA or 218 atm).

As the substance approaches critical temperature, the properties of its gas and liquid phases converge, resulting in only one phase at the critical point: a homogeneous supercritical fluid."

en.wikipedia.org/wiki/Critical_point (thermodynamics). This phenomenon is illustrated in FIG. 4.

Accordingly, unlike and even contrary to the prior art, the present invention takes advantage of the principle of "dense" phase or supercritical phase behavior for sampling, providing a system and method of extracting a "dense" phase sample, conditioning same for measurement or other purpose.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein:

FIG. 3 is a Soave-Redich-Kwong EOS Phase Wizard Data Sheet illustrating the phase change of the same components of FIG. 2 at the increased inlet pressure of 616.99 PSIA (605.29 PSIG), same 60 degrees F. temperature, but comprising 80% gas and 20% liquid.

DETAILED DISCUSSION OF THE INVENTION

Figure 1:
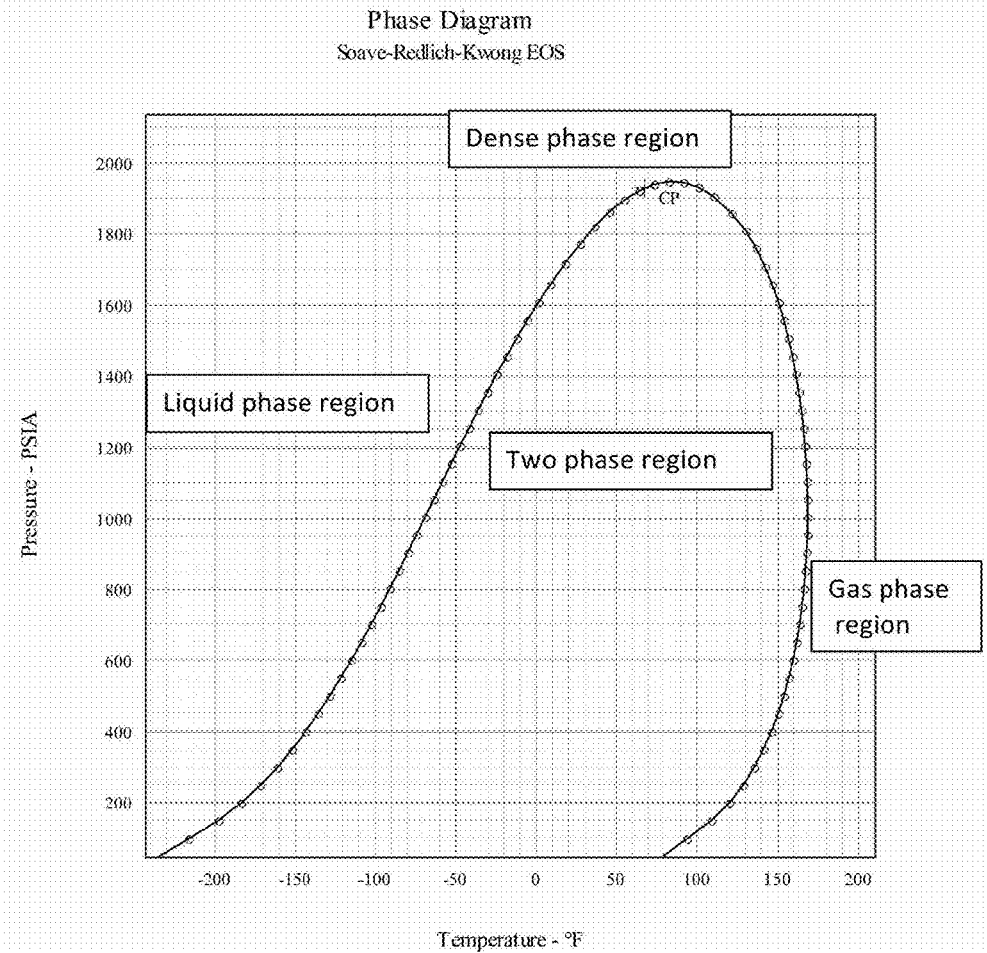
FIG. 1 is a Soave-Redich-Kwong EOS chart illustrating four phase regions of an exemplary sample hydrocarbon fluid stream sample composition at varying pressure and temperature.
Figure 2:
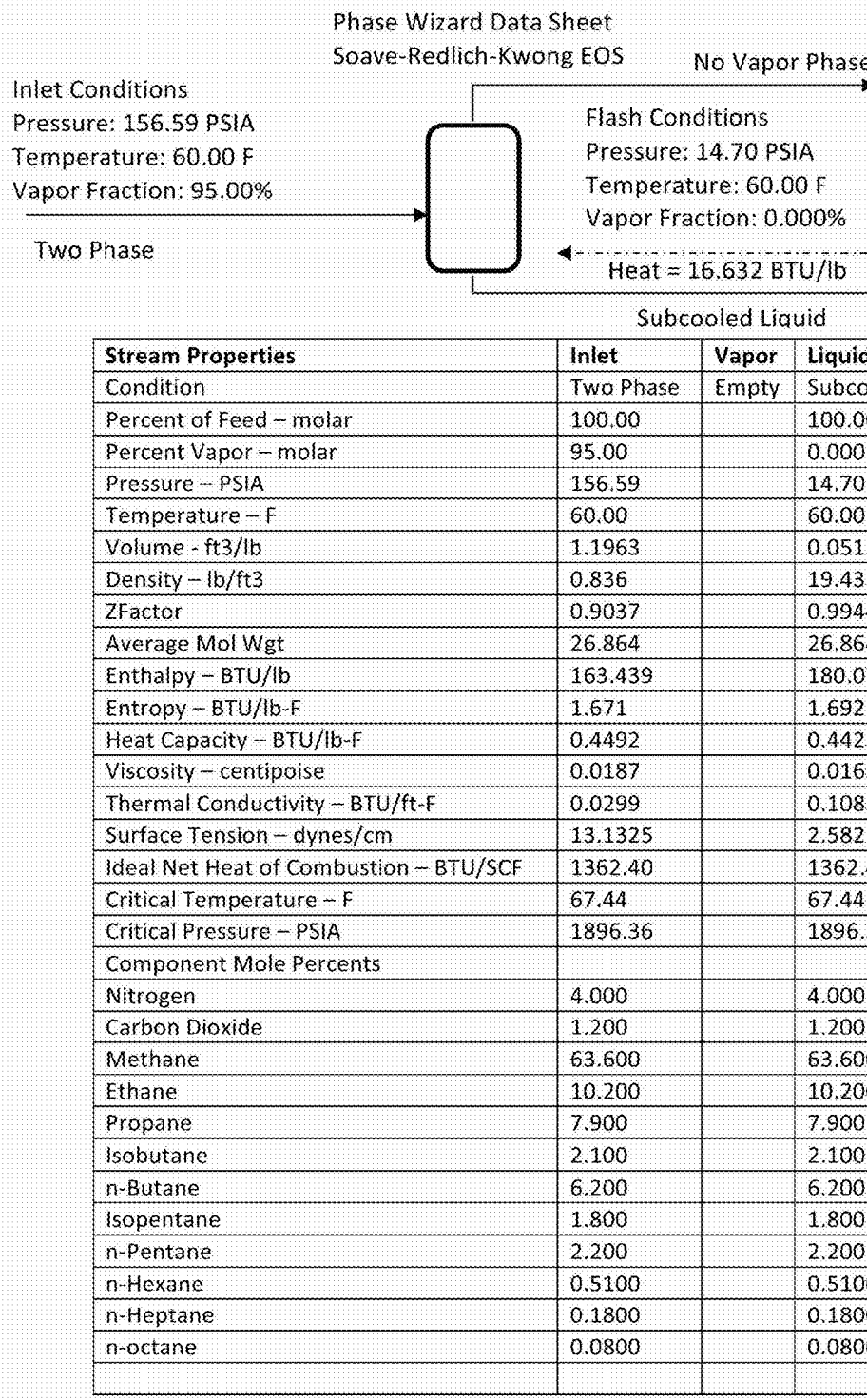
FIG. 2 is a Soave-Redich-Kwong EOS Phase Wizard Data Sheet illustrating the phase change of the components of FIG. 1 at an exemplary inlet pressure P of 156.59 PSIA (141.89 PSIG) and temperature T of 60 degrees F., showing 95% gas and 5% liquid.
Figure 4:
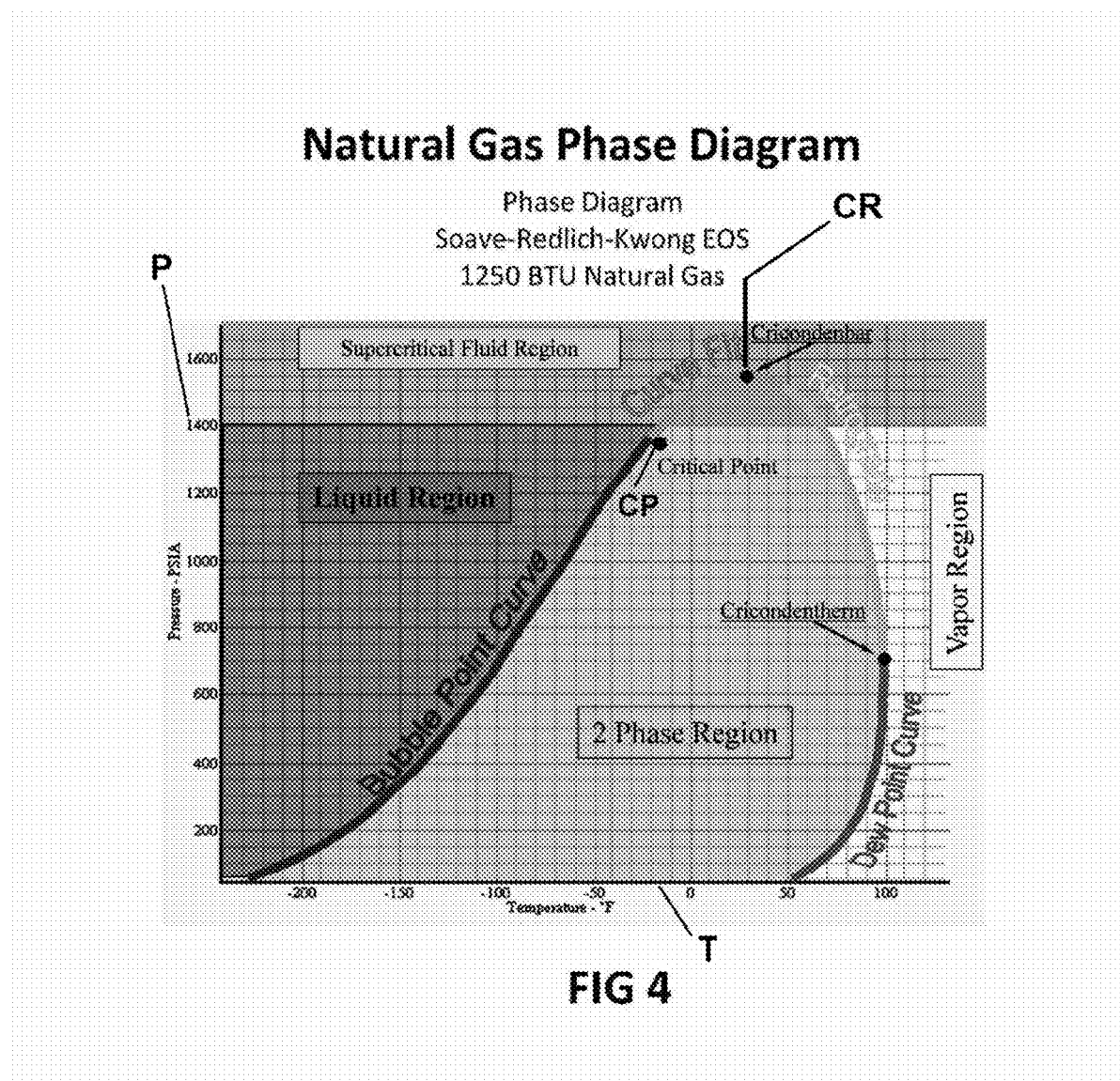
FIG. 4 is an exemplary Natural Gas phase diagram illustrating the various phase regions for an exemplary composition comprising 1250 BTU Natural Gas, on a pressure P and temperature T curve, illustrating the transition point from liquid phase to supercritical or dense phase (or visa-versa), otherwise known as the criticality point CP, as well as the cricondenbar CR and Cricondentherm CM points and associated vapor phase region.

In contrast to the use of mechanical separation or commingling of the multiphase fluid stream to form a homogenous fluid for sampling purposes, the preferred embodiment of the present invention seeks to exploit the dense phase in a wet or multiphase fluid stream or sample by analyzing same to discern its discrete components, such as via EOS software data, to indicate the temperature and pressure required to push the multi-component sample to be dense phase, so as to provide an inherently homogenous, multi-component composition, while dispensing with the necessity of mechanically mixing, separating, filtering, or otherwise attempting to separate liquid(s).

Under the preferred embodiment of the present invention, treating the sample to facilitate its transition to dense phase may require the conditioning of same to higher temperatures and/or pressures to flash it to said dense phase, the particulars of which could be derived from the EOS phase diagram data, or determined via other conventional means.

Said EOS phase program data need not necessarily be required each time a sample is taken, rather said data may be, depending upon the circumstances, historical data from the particular site, or other reference source. Alternatively, said EOS phase program data may be required for new sites, or when there are changes in the fluid stream, or newly sampled data using spot sampling methods may be otherwise be required. Bottom line, the EOS phase program is an example of a means to acquire the information to determine how to bring the fluid sample into dense phase for sampling purposes.

Depending upon the composition and environmental variables, the forced transition of a sample from multiphase to dense phase utilizing the EOS phase program may require unique or customized heating and/or pressurizing equipment reliably ensure the sample is transitioned above the critical point to dense phase. Since there could be errors in the samples taken in used or even in the software used, a buffer zone might be advantageous to target the sample above the critical point to ensure dense phase transition, i.e., not just barely above the critical point. A buffer zone of 30 degrees F., for example, could be sufficient for many, if not most applications.

In the first, preferred embodiment of the present invention, the components of interest of the sample are already in the dense phase. For reasons discussed above, this condition is outside the scope of industry standards for sampling, i.e., industry standards would suggest the use of the EOS software to verify that the sample is single phase (gas phase only).

Applicant is unaware of any prior art teaching, contemplating or otherwise suggesting the use of EOS software for the reason of confirming the sample is dense phase for purposes of sampling same as a homogenous fluid, as the industry standards world-wide, as understood and discussed supra, is believed to only utilize said software to ensure the exclusion of dense sampling.

In contrast, the present invention exploits the use of phase diagram software (EOS) such as used in the examples described above, to, where required, manipulate the sample to place same in dense phase, and/or verify that the sample is in the dense phase condition (a homogenous fluid outside the scope of industry standards) so as to provide a superior sample over present/prior techniques.

Founded in 1901, NIST (National Institute of Standards and Technology) is a non-regulatory federal agency within the U.S. Department of Commerce. NIST's mission is to promote U.S. innovation and industrial competitiveness by advancing measurement science, standards, and technology in ways that enhance economic security and improve our quality of life.

NIST Standard Reference Database 23 includes the NIST Reference Fluid Thermodynamic and Transport Properties Database (REFPROP): Version 9.1. The REFPROP "database" is actually a program and does not contain any experimental information, aside from the critical and triple points of the pure fluids. The program uses equations for the thermodynamic and transport properties to calculate the state points of the fluid or mixture. These equations are the most accurate equations available worldwide. Their high accuracy is obtained through many coefficients in the equations, and thus the calculation speed will be slower than other equations such as the Peng-Robinson cubic equations.

These equations are generally valid over the entire vapor and liquid regions of the fluid, including supercritical states. The Source code, FORTRAN subroutines, and associated fluid data files are provided for those wishing to access REFPROP calculations from their own applications. The present inventions utilize a custom hardware recommendation software program that uses those inputs to determine the exact hardware needed for the application.

The web page at www.nist.gov/srd/nist3.cfm indicates: "Source code: The FORTRAN subroutines and associated fluid data files are provided for those wishing to access REFPROP calculations from their own applications . . . Excel spreadsheets: A sample spreadsheet is included that demonstrates how the REFPROP DLL can be linked to Excel. Most properties that are available in the graphical interface can also be calculated in the spreadsheet".

Figure 10:
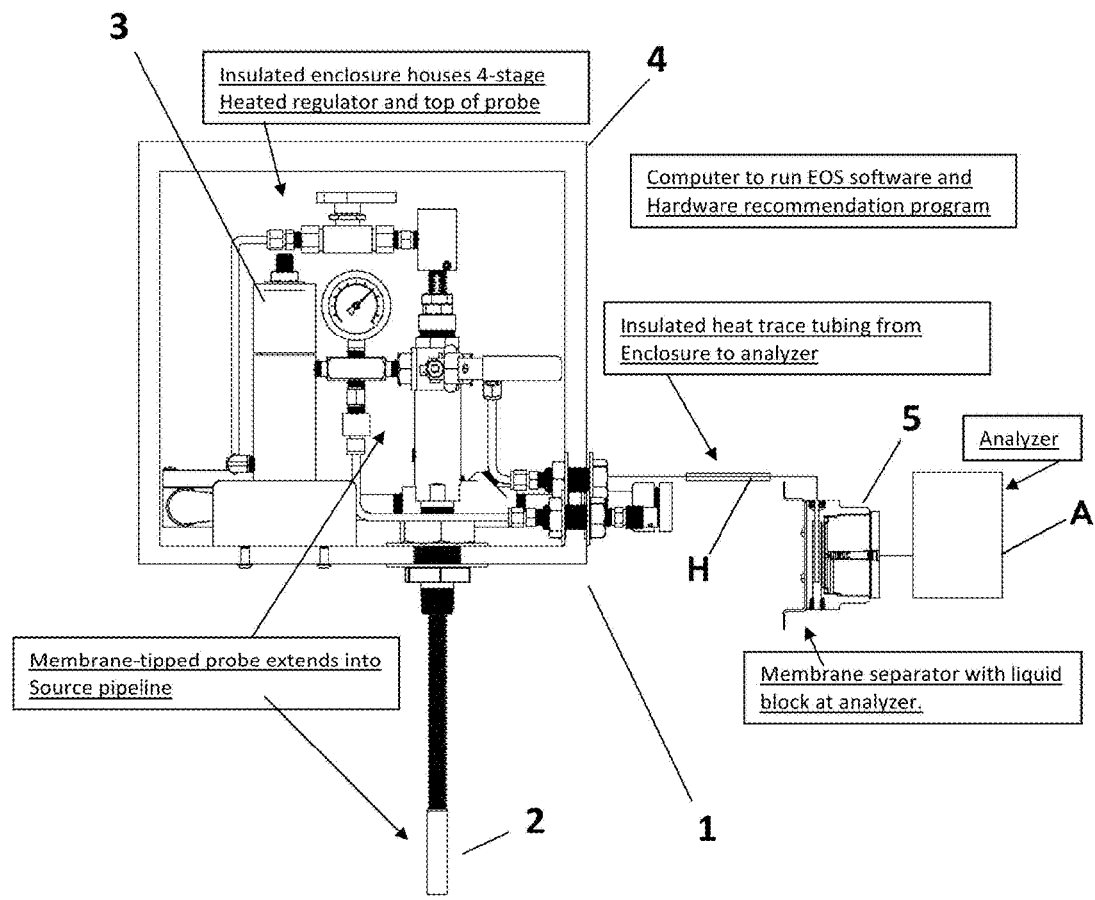
FIG. 10 is a side view of an exemplary sampling system in line drawing form including a thermally-insulated enclosure with heated regulator and other components in accomplishing the method of FIG. 9.

Continuing with FIG. 10, illustrating the system of preferred embodiment of the present invention, an exemplary system 1 for collecting and processing the sample under the present invention is shown and may comprise, for example, a sample probe 2 for insertion into a fluid stream, and a multistage regulator 3 (such as the A+ Corporation JTR—Mayeaux U.S. Pat. No. 8,220,479) which may be heated or non-heated, preferably in an enclosure 4 insulated or heat traced tubing. A membrane separator 5 with liquid block option (Mayeaux U.S. Pat. No. 7,555,964) such as the A+ Corporation Genie is used before the measurement device to ensure that no liquid interferes with the measurement.

In the present example, EOS phase diagram software 6 is used to confirm that the sample is in the dense phase (a homogenous fluid), thereby, under the present invention, providing verification that no mechanical mixing or isokinetic sampling of a two phase sample is required.

A custom hardware recommendation software program 7 (FIG. 9) or other guidance can be utilized to determine the exact hardware selection of regulation stages/ranges/setpoints and temperature required to lower the pressure of the dense phase " . . . so that a vapor only industry standard sample can be transported to the analyzer" (FIG. 9), without allowing any liquid to form (i.e., preventing retrograde condensation and keeping the sample out of the two-phase portion of the phase diagram). A+ Corporation of Gonzales, LA provides such hardware recommendation services, via its website at: www.geniefilters.com/services/phase-diagrams/

In some cases, man-made injected chemicals such as glycols or scavengers may not be in the dense phase, since they are radically different components. In those cases, membrane technology such as the Genie Membrane-tipped probe (Mayeaux U.S. Pat. No. 6,357,304) may be used in the dense phase to remove the man-made injected chemicals that are in the liquid phase, and not in the dense phase. A membrane separator with liquid block option (Mayeaux U.S. Pat. No. 7,555,964) such as the A+ Corporation Genie is provided in the fluid flow prior to the measurement device to ensure that no liquid interferes with the measurement, as shown in FIG. 10.

Figure 5:
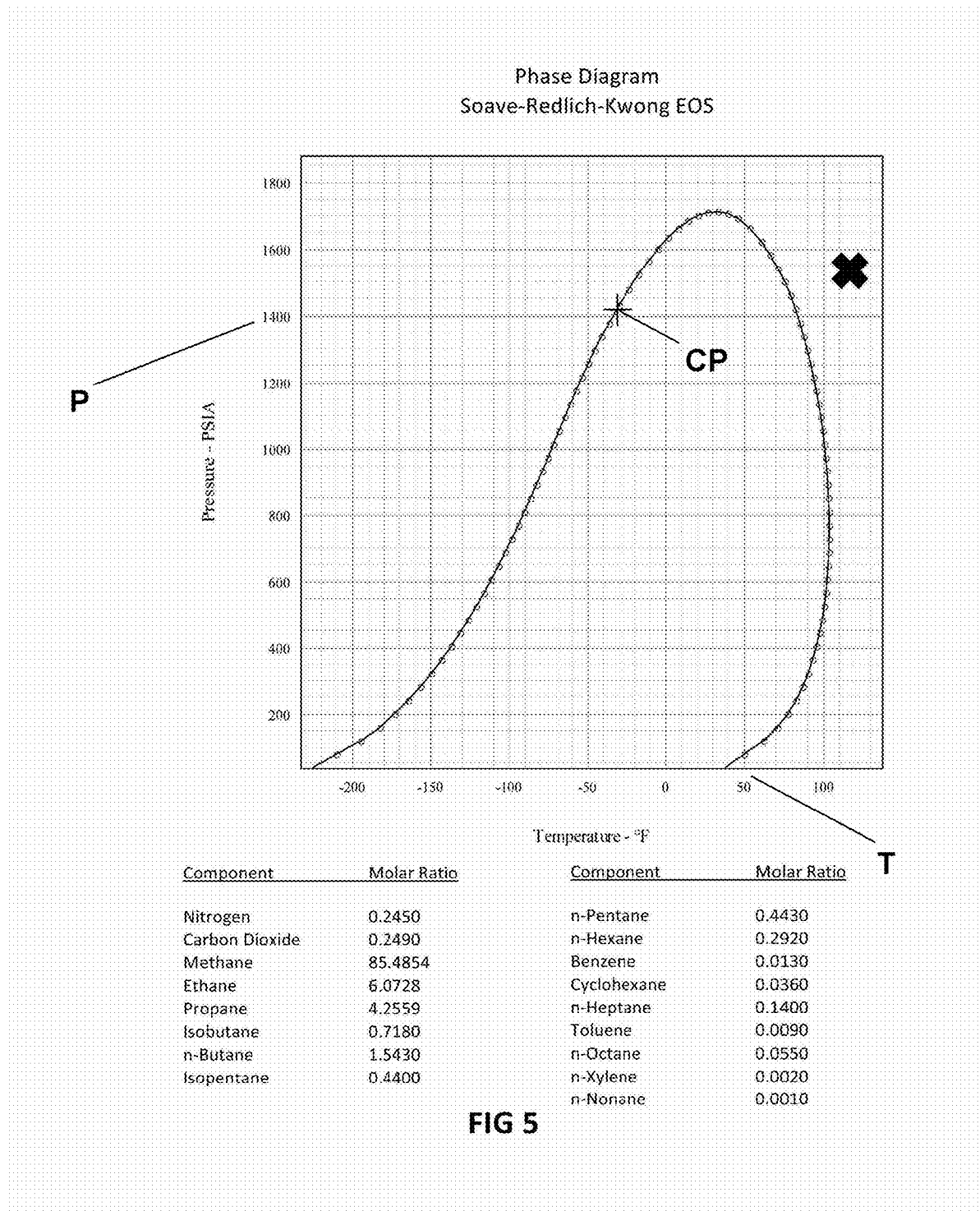
FIG. 5 is a phase diagram showing an exemplary phase position and curve for the indicated composition, and the associated criticality point (CP), at a given pressure P and temperature T.
Figure 6:
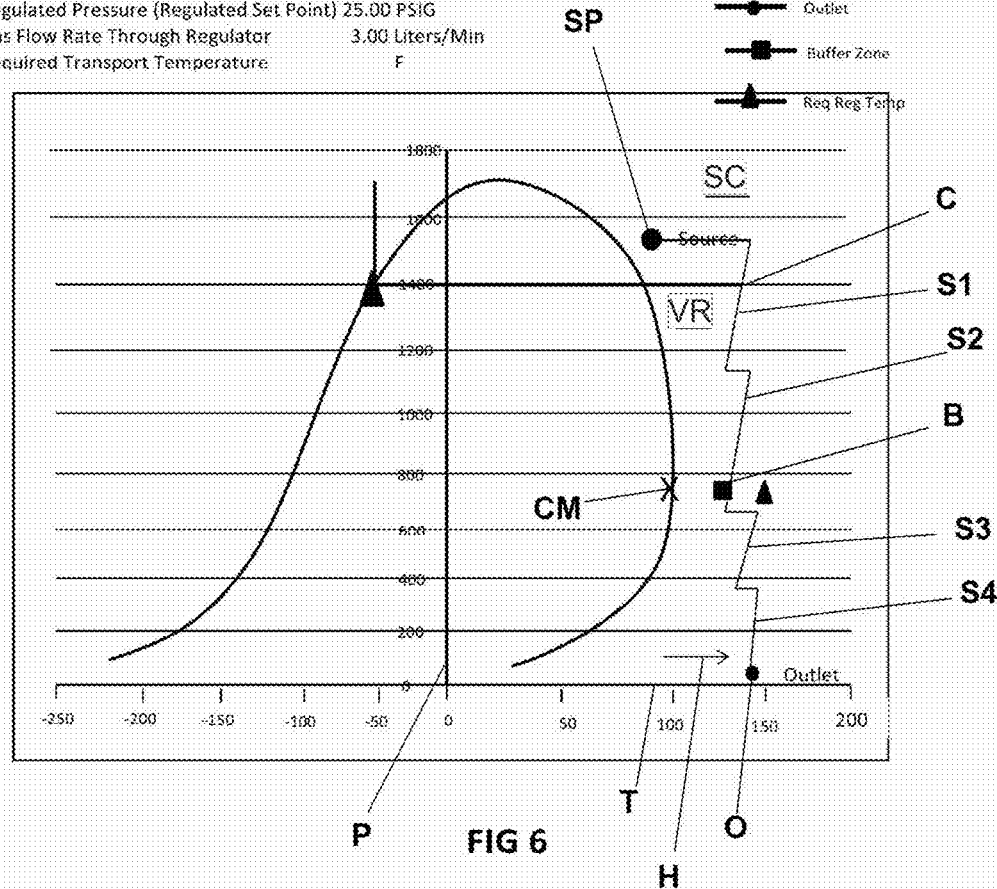
FIG. 6 is an exemplary read-out of an automated hardware recommendation software for the fluid composition of FIG. 5 relating to a dense phase sample extracted from a fluid stream using a membrane tipped probe, and the exemplary recommended staged or incremental pressure reduction utilizing a 4-stage, heated regulator for the sample, from the source pressure SP of 1525 PSIG and temperature T of 94.00 F in the supercritical zone SC, to a first stage 51 drop through Critical Pressure C of 1407.53 PSIG (and from supercritical or dense phase to vapor-only phase in the vapor region VR), a second stage S2 pressure drop through the 753.77 PSIG Cricondentherm CM Pressure above 103.96 F temperature (via heat H adjustment utilizing the heated regulator) condition the sample to the buffer zone B criteria for vapor only phase. A further, two-stage (S3, S4) staged pressure drop is then provided (by third and fourth stages of the 4-stage regulator, respectively) so that the homogenized sample is adjusted to the reduced outlet O pressure P, to provide a lower manageable pressure for flow of sample in an industry standard, vapor only phase to an analyzer, while avoiding retrograde condensation.
Figure 7:
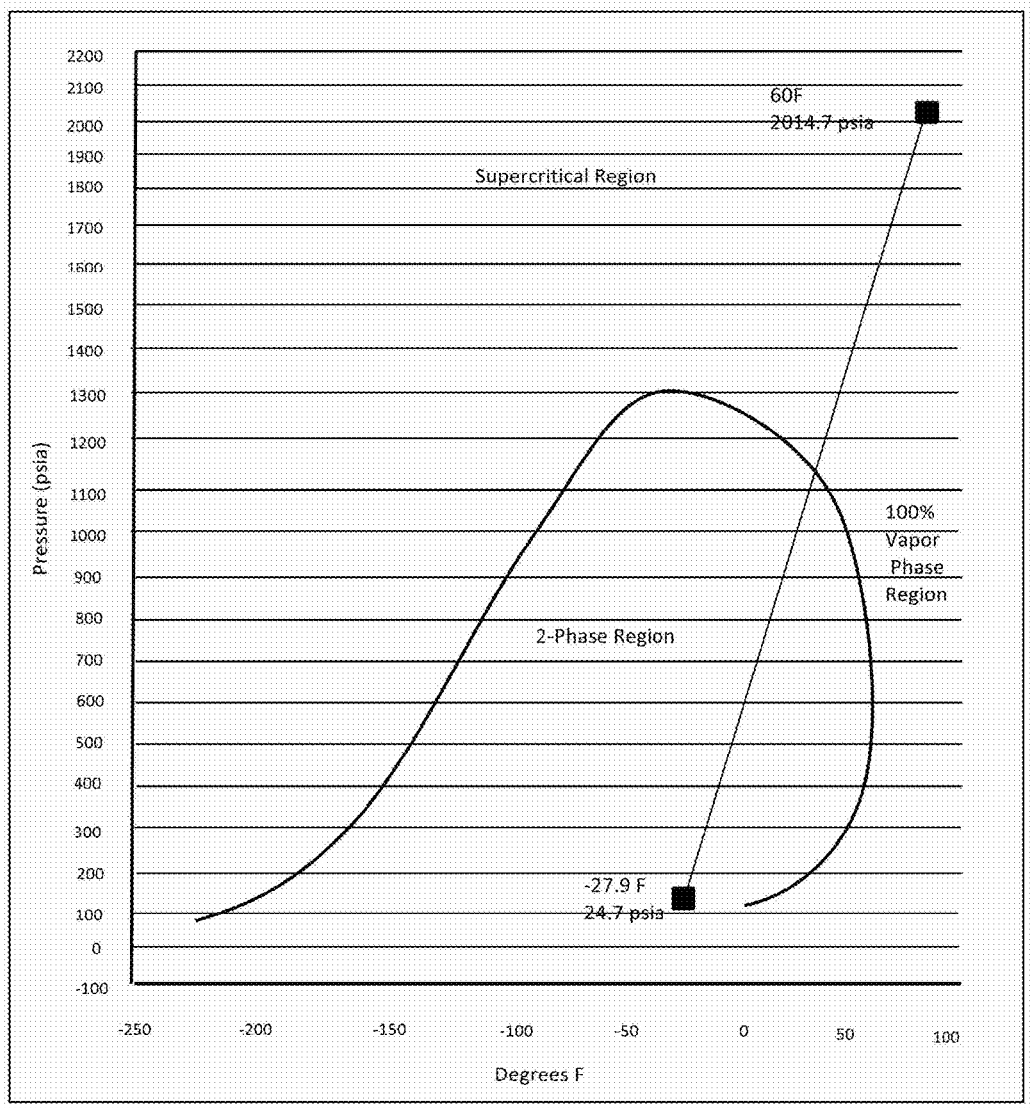
FIG. 7 is a pressure/temperature graph illustrating the undesired consequences of using a conventional, single-stage regulator in the present application to drop the supercritical sample pressure to a lower analyzer pressure, resulting in migration of the sample into the undesired two phase region and distorting the sample, due to excessive single-stage pressure drop and associated retrograde condensation. This is opposed to the methodology of the present invention, (which uses the A+ custom hardware selection software for recommending proper hardware and layout, shown in FIG. 6) which would result in the sample being brought from above the critical point (the dense phase region) to the desired, reduced analyzer pressure (10 PSIG in this case) in the desired vapor phase using incremental pressure reduction so as to avoid retrograde condensation.

A first embodiment of the present invention, detailing steps to be accomplished in taking a dense phase sample may be summarized as comprising the following:
1) Determining fluid stream components utilizing EOS Software output from historical, material balance, spot sample data input, or other methodology, for example, as shown in FIG. 5, providing composition data;
2) Verifying the source to be dense phase (above the critical point) (as in FIG. 6) so as to bypass mechanical mixing and ensure components of interest will be in one single phase—the dense phase;
3) Utilizing said composition data to formulate a custom hardware layout and configuration, or utilizing a custom software program to analyze said composition data (as shown in FIG. 6) to provide a custom hardware layout recommendation, determine the exact hardware selection of regulation stages/ranges/setpoints and temperature required to lower the pressure of the dense phase without allowing any liquid to form (preventing retrograde condensation and keeping the sample out of the two-phase portion of the phase diagram);
4) Utilizing the guidelines in step 3 to provide the hardware and required parameters for sampling. In the present example, the custom software program (FIG. 6) recommends a membrane-tipped probe to reject man-made chemicals such as glycols, amines, etc. that might be present in the source inside the pipeline that are not in the dense phase. Those components are not components of interest and will not be analyzed. They will be rejected inside the pipeline at the source by the membrane-tipped probe.
5) In the present example, a 4-stage insulated and heated regulator with a temperature of 134 degrees F. (cricondentherm temperature of 103.96+prior discussed buffer zone of 30=134 F) is required to drop the source pressure from 1,525 PSIG to the required analyzer inlet pressure of 25 PSIG, as shown in FIG. 6. Note: if this custom hardware selection guide would not be used, a single-stage conventional regulator would likely have been used by default and the sample would have crossed into the 2-phase region thus distorting the sample before it could be analyzed as seen in FIG. 7.
6) Insulated Heat traced tubing is used to transport the sample to the analyzer.
7) A membrane separator with liquid block option 5 is installed at the gas analyzer to protect said gas analyzer A (FIG. 10) from liquids that could condense out if the heat trace H fails.

In another embodiment of the present invention, detailing steps for use when the sample is in a two phase region, may be accomplished as follows.
1) Analyzing the composition, for example via EOS software, confirming that the sample is in the two phase region; then
2) Treating the two phase sample, in this case either via heating with a temperature increasing device and/or pressurizing with a pressure increasing device so that the sample is moved out of the two phase portion of the phase diagram and above the critical point so as to transition to a dense phase sample.

As discussed, this technique is radically different from mechanically homogenizing or mixing a two phase sample to the point of perfection, which can be very difficult or even impossible using current equipment.

The above method solves the problem of mixing or separating by eliminating the need for it completely. As stated earlier, a dense phase sample, by its very nature, is homogenized, thereby dispensing with the need for a mechanical or static mixer or separator. To reiterate, the many different dynamic, changing flow patterns make homogenous mixing for isokinetic sampling two phase wet gas very difficult—different phases, different liquids, different surface tensions, different viscosities, different velocities . . . hydrocarbon liquids, water, glycols, scavengers, etc.

In some cases, man-made injected chemicals such as glycols or scavengers may not go supercritical when the components of interest sample goes supercritical. Those contaminates can be removed from the supercritical sample before the analysis using membrane technology such as the Genie Membrane-tipped probe. The main sample stream or a slip-stream such as a meter run could be utilized with the temperature increasing or pressure increasing device. The temperature increasing device could be as simple as a conventional heater with insulation, heat trace with insulation, or a custom developed solution. The pressure increasing device could be as simple as a compressor, pump, or booster or it could be a custom developed device.

The present invention would use the dense phase behavior to present a uniform homogenous sample that is not a multiphase sample. The problem with current mixers or trying to homogenize samples with different types of liquid, forms of liquid, etc. is eliminated by this method. The problems of trying to measure the dry gas flow and the liquid flow are eliminated. The problems of matching velocities for isokinetic sampling are eliminated.

Figure 8:
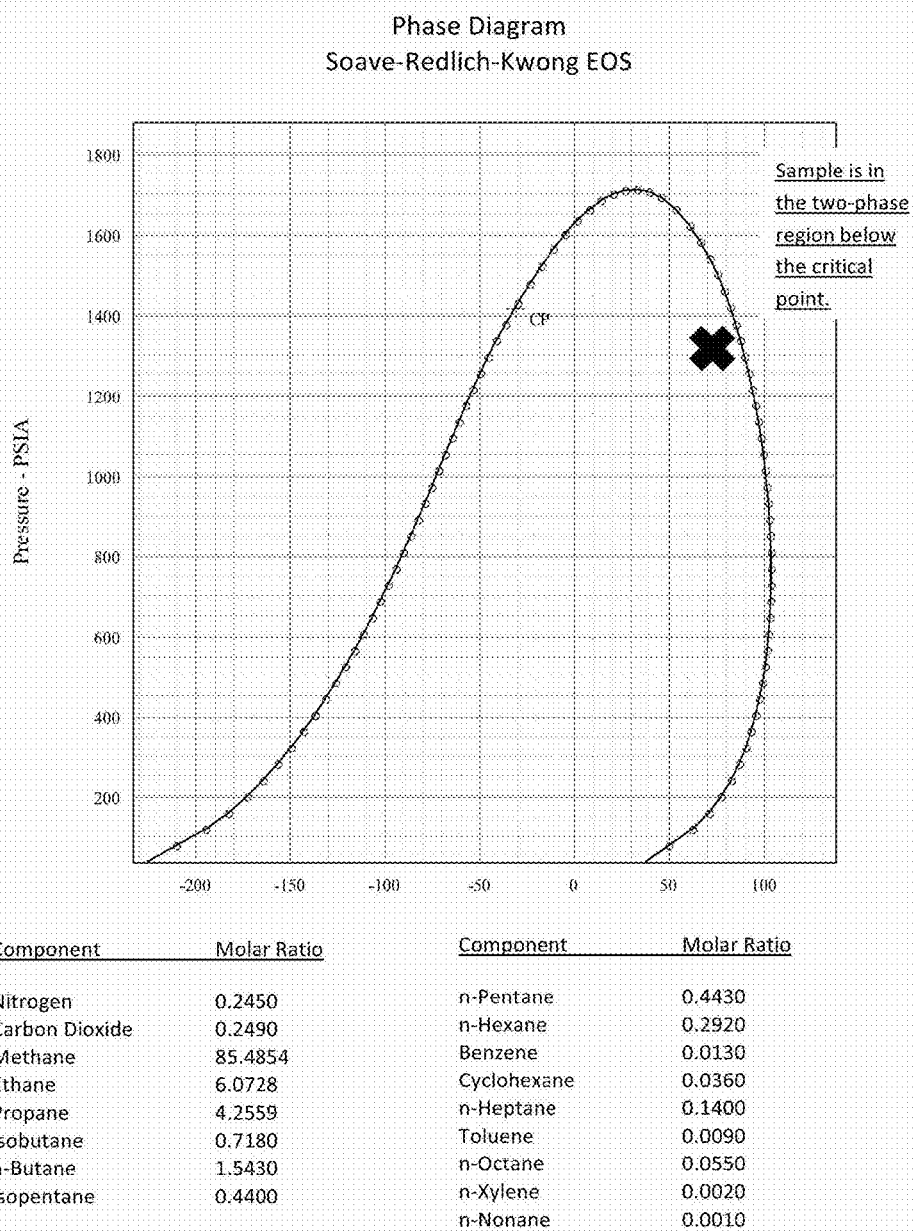
FIG. 8 illustrates an exemplary composition in the two-phase region, and below the critical point (CP).
Figure 11:
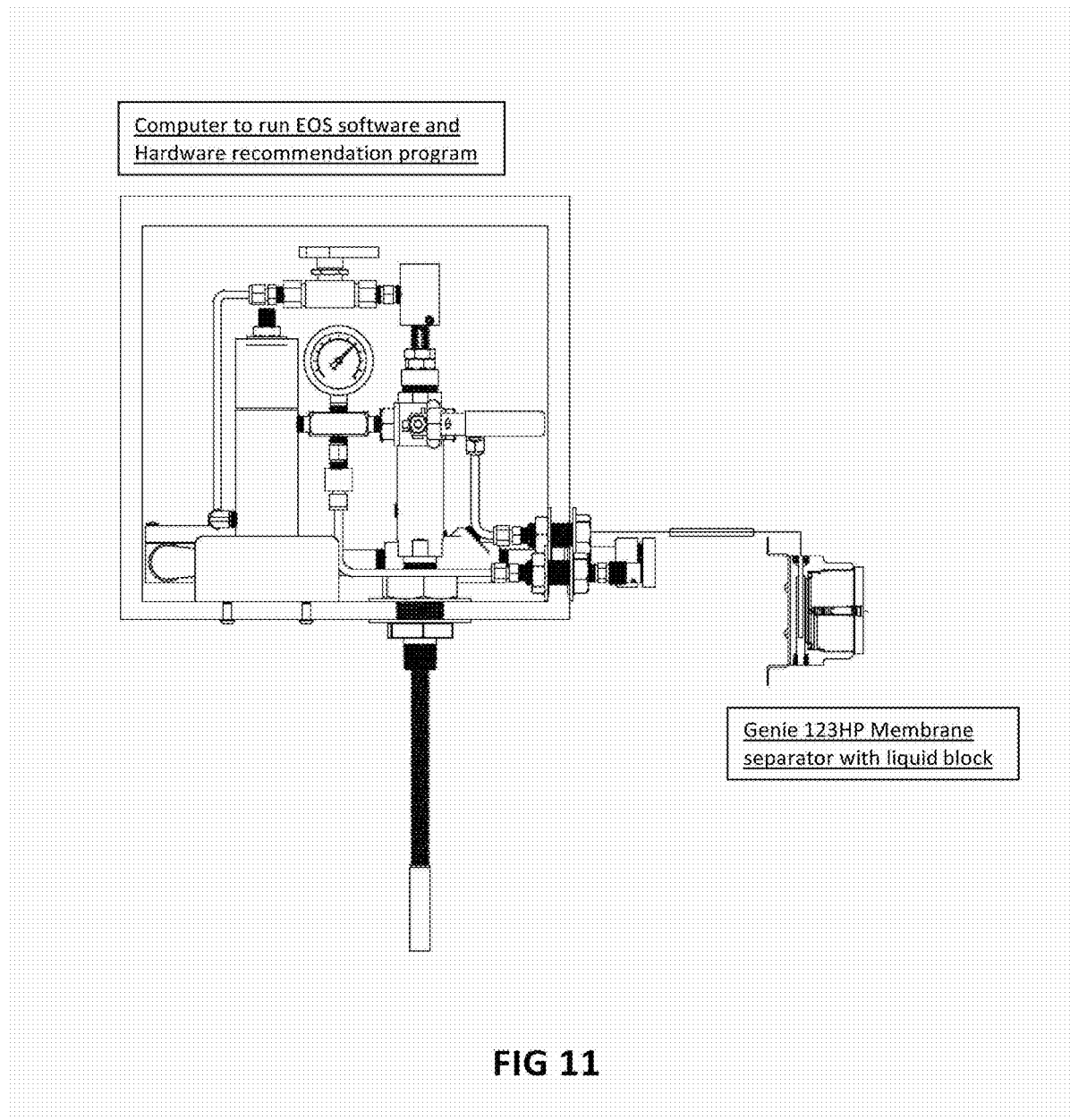
FIG. 11 is another view of the system of FIG. 10.

For another example of a methodology under the present invention, assuming the fluid stream similar to that above, but a source pressure below 1,408 PSIG and the temperature of 75 degrees F., one could:

1) Analyze the fluid stream, for example, via EOS Software output, from historical, material balance or spot sample data input, to provide phase and compositional data, as shown in FIG. 8.
2) Based upon the data, the multi-component fluid source is then treated or adjusted, in this example, via temperature increasing device such as a heater, and/or a pressure adjusting device, for example, as a reducing or regulating device such as a regulator (eg, a multistage regulator 3 as in FIG. 10), and/or a pressure increasing device D (FIG. 9) such as a compressor or pump, to adjust the temperature/pressure above the critical point indicated on the EOS software, as required so as to flash same to dense phase, respectively.
3) The source is then verified to be dense phase (above the critical point). If such is the case, no mechanical mixing is required and all components of interest will be in one phase . . . the dense phase.
4) Determining hardware to be utilized, for example, via Hardware Recommendation program is run (discussed with FIG. 6).
5) In this case, A membrane-tipped probe is required to reject manmade chemicals such as glycols, amines, etc. that may be present in the source inside the pipeline that are not in the dense phase. Those components are not components of interest and will not be analyzed. They will be rejected inside the pipeline at the source by the membrane-tipped probe.
6) A 4-stage insulated and heated regulator with a temperature of 134 degrees F. (cricondentherm temperature of 103.96+buffer of 30=134 F) is determined to be required to drop the source pressure from 1,525 PSIG to the required analyzer inlet pressure of 25 PSIG as shown in FIG. 6. Note: if this custom hardware selection guide would not be used, then a single-stage conventional regulator would have been used by default and the sample would have crossed into the 2-phase region, thus distorting the sample before it could be analyzed (see FIGS. 10 & 11).
7) Using insulated heat traced tubing to transport the sample to the analyzer.
8) a membrane separator with liquid block option is installed at the analyzer to protect the gas analyzer from liquids that could condense out if the heat trace fails.

Figure 9:
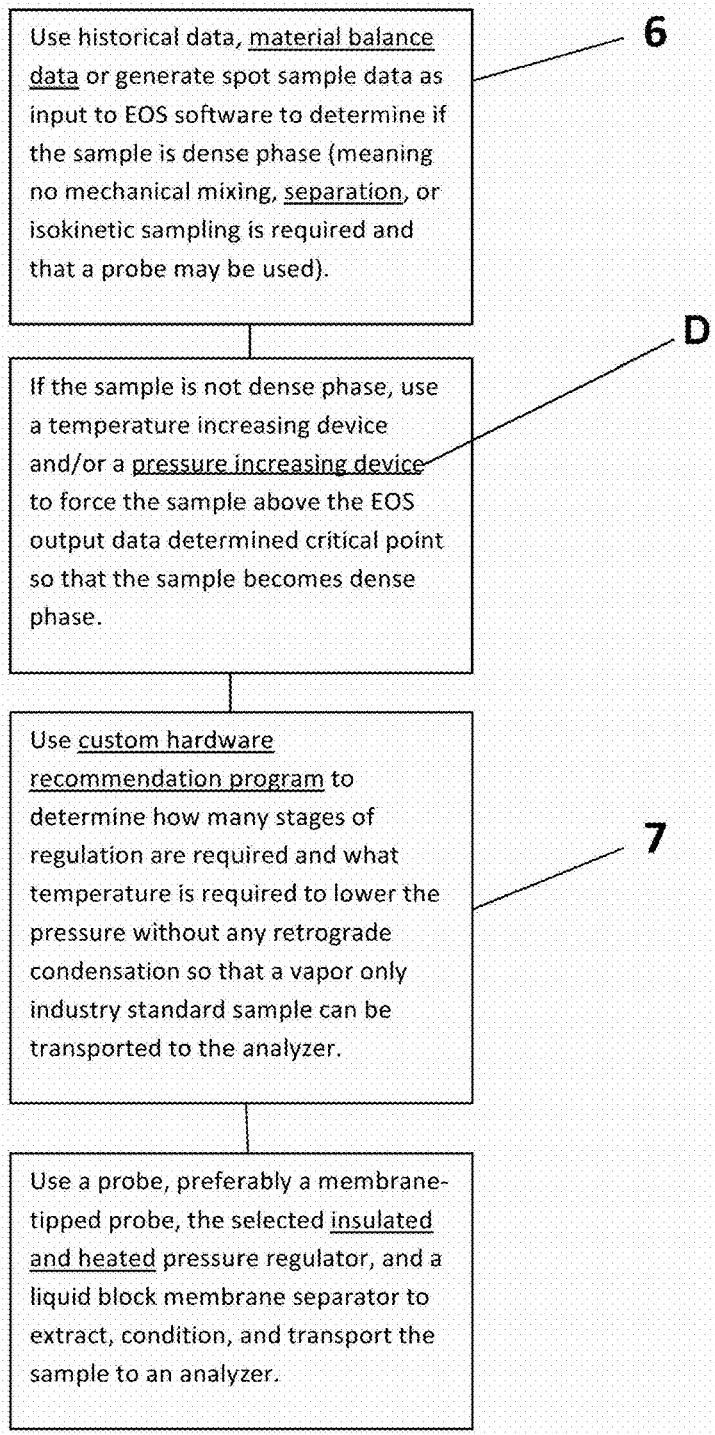
FIG. 9 is a flow chart illustrating an exemplary method of the present invention of analyzing a fluid specimen.

Exemplary steps in performing a methodology of the present invention may be further found in FIG. 9.

Options

Heated regulator is powered off any existing heat trace where desired/required.

The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

I claim:

1. A method of preparing a sample of a fluid for analysis, comprising the steps of:
   a) providing data relating to said fluid to EOS software to provide a guideline as to determine the phase of said fluid as well as providing data for forced transition to dense phase of said fluid in the form of temperature and/or pressure criteria if said fluid is multiphase;
   b) if said fluid is multiphase, adjusting the pressure and/or temperature of said sample utilizing pressure and or temperature adjusting equipment, respectively, as required, to reach said temperature and pressure criteria, so as to facilitate transition of said multiphase fluid to a dense phase, providing a homogeneous sample;
   c) flowing said homogeneous sample to an analyzer.

2. The method of claim 1, wherein step "b" further comprises the sub-step b(i) of heating said sample with a heater and adjusting the pressure of said sample utilizing said pressure adjusting equipment, as required, to reach said temperature and pressure criteria, respectively, to facilitate transition of said multiphase fluid to said dense phase.

3. The method step of claim 1, wherein in step "b" the pressure of said sample is adjusted via a pressure increasing device.

4. The method of claim 3, wherein said pressure increasing device comprises a compressor, pump or booster.

5. The method of claim 1, wherein said pressure adjusting equipment comprises a multi-stage regulator.

6. The method of claim 5 wherein:
   after step "b(i)" there is provided the added step of:
      b(a). reducing said pressure and temperature of said homogeneous sample as required to facilitate transition of said sample from dense phase to vapor-only phase, utilizing said multi-stage regulator to provide staged pressure reduction so as to prevent retrograde condensation, providing a reduced pressure, vapor-only phase sample;
   wherein said reduced pressure, vapor only phase sample comprises said homogeneous sample of step "c".

7. The Method of claim 6, wherein in step b(a), said sample is heated as required by heating said multi-stage regulator.

8. The method of claim 6, wherein after step b(a) there is provided the additional steps of "b(b)" providing a membrane separator with liquid block upstream said analyzer, and "b(c)" flowing said reduced pressure, vapor-only phase sample through said membrane separator, isolating any residual liquid phase fluids from said reduced pressure, vapor-only phase sample.

9. The method of claim 6, wherein in step "c" said analyzer comprises a gas analyzer.

10. The Method of claim 9, wherein in step b(i), said sample is heated by heating said regulator.

11. The method of claim 10, wherein step b(i) further comprises the step of: adjusting the temperature of said sample to a pre-defined buffer zone above the point of phase change to dense phase, providing a dense phase sample.

12. The method of claim 11, wherein in step "b" there is provided the added step of using a probe to obtain said fluid from a source, and utilizing said probe to facilitate flow of said fluid to said regulator.

13. A method of preparing a fluid from a source for analysis, comprising the steps of:
   a) determining the phase of said fluid by inputting data relating to said fluid to EOS software, providing EOS output;

b) if said fluid is multiphase, utilizing said EOS output to provide a temperature and pressure criteria for transition of said multiphase fluid to dense phase;

c) adjusting the temperature and pressure of said fluid utilizing a temperature increasing device and/or a pressure adjusting device as required to facilitate said fluid to reach said temperature and pressure criteria, to facilitate the transition of said fluid to dense phase;

d) utilizing said properties of dense phase to homogenize said fluid, providing a homogenized sample;

e) reducing said pressure of said homogenized sample in stages using one or more regulators, providing a reduced pressure homogenized sample;

f) flowing said reduced pressure homogenized sample to an analyzer; and g) analyzing said reduced pressure homogenized sample without mixing or separating.

14. The method of claim 13, wherein in step "e", said temperature and pressure of said homogenized sample is adjusted by a multi-stage pressure regulator.

15. The method step of claim 13, wherein in step "c" the said pressure adjusting device comprises a pressure increasing device.

16. The method of claim 15 wherein pressure increasing device comprises a compressor, pump or booster, to increase the pressure of said sample.

17. A method of preparing a fluid from a source for analysis, comprising the steps of:

a) determining the phase of said fluid by inputting data relating to said fluid to EOS software, providing EOS output;

b) if said fluid is multiphase, utilizing said EOS output to provide a temperature and pressure criteria for transition of said multiphase fluid to dense phase;

c) adjusting the temperature and pressure of said fluid utilizing a temperature increasing device and/or a pressure adjusting device as required to facilitate said fluid to reach said temperature and pressure criteria, to facilitate the transition of said fluid to dense phase;

d) utilizing said properties of dense phase to homogenize said fluid, providing a homogenized sample, comprising the sub-steps of;

d(1) reducing said pressure and adjusting said temperature of said fluid as required to facilitate transition of said fluid from dense phase to vapor-only phase; then d(2) further reducing said pressure of said fluid in stages, so as to prevent retrograde condensation, providing a reduced pressure, vapor-only phase homogeneous sample;

e) flowing said homogeneous sample to an analyzer.

18. The invention of claim 17, wherein in step "c" said fluid temperature and pressure is adjusted at said source, providing a dense phase source, and in step "d" there is provided the sub-step of utilizing a probe to extract a sample of said dense phase source to provide said homogeneous sample.

19. A method of preparing a fluid from a source for analysis, comprising the steps of:

a) determining the phase of said fluid by inputting data relating to said fluid to EOS software, providing EOS output;

b) if said fluid is multiphase, designating said fluid as multiphase fluid and utilizing said EOS output to provide a temperature and pressure criteria for transition of said multiphase fluid to dense phase;

c) if said fluid is dense phase, designating said fluid as dense phase fluid and proceeding to step "e";

d) adjusting the temperature and pressure of said multiphase fluid utilizing a temperature increasing device and/or a pressure adjusting device as required to facilitate said fluid reaching said temperature and pressure criteria, to facilitate the forced transition of said multiphase fluid to dense phase, providing said dense phase fluid;

e) utilizing said properties of dense phase to homogenize said dense phase fluid;

f) reducing said pressure and adjusting said temperature of said dense phase fluid as required to facilitate transition of said dense phase fluid to vapor-only phase, providing a high pressure, homogeneous, vapor-only phase fluid;

g) further reducing said pressure of said high-pressure, homogeneous, vapor-only phase fluid in stages so as to prevent retrograde condensation, while adjusting temperature as required, providing a reduced pressure, homogeneous, vapor-only phase fluid sample;

h) flowing said reduced pressure, homogeneous, vapor-only phase fluid sample to an analyzer.

20. The method of claim 19, wherein in step "d" said step of adjusting said pressure of said multiphase fluid comprises the step of compressing said multiphase fluid with a compressor to said pressure criteria of step "b".

21. The method of claim 20, wherein in step "d" said step of adjusting said temperature of said multiphase fluid comprises the step of heating said multiphase fluid with a heater to said temperature criteria of step "b".

22. The method of claim 19, wherein a regulator is utilized to provide pressure reduction in steps "f" and "g".

23. The method of claim 22, wherein in step "g" said regulator comprises a heated, multi-stage regulator configured to provide staged pressure reduction.

24. The method of claim 23, wherein there is further provided in step "g" the added step of determining how many stages are required, and what temperature is required to facilitate said further reduction in pressure without retrograde condensation.

25. The method of claim 24, wherein said step of determining how many stages are required and what temperature is required is accomplished by a computer program.

26. The method of claim 22, wherein there is further provided in step "e" the added step of extracting said dense phase fluid from said source utilizing a probe, and flowing same to said regulator.

27. The method of claim 26, wherein said probe comprises a membrane-tipped probe, and there is included in step "e" the added step of flowing said dense phase fluid through said membrane so as to prevent the passage of liquid therethrough.

* * * * *